United States Patent [19]

Neuzil et al.

[11] 4,119,678
[45] Oct. 10, 1978

[54] DESORBENT FOR SEPARATION OF BUTENE-1 FROM A C4 HYDROCARBON MIXTURE USING ZEOLITE X

[75] Inventors: Richard W. Neuzil, Downers Grove; Richard L. Fergin, Mt. Prospect, both of Ill.

[73] Assignee: UOP Inc., Des Plaines, Ill.

[21] Appl. No.: 815,041

[22] Filed: Jul. 12, 1977

[51] Int. Cl.$^2$ ............................................. C07C 11/12
[52] U.S. Cl. .............................. 260/677 A; 208/310.2; 260/677 AD
[58] Field of Search .................. 260/677 A, 677 AD; 208/310.2

[56] References Cited

U.S. PATENT DOCUMENTS

| 3,723,561 | 3/1973 | Prieqnitz ........................ 260/677 A |
| 3,969,223 | 7/1976 | Rosbeck et al. ............. 260/677 AD |

*Primary Examiner*—C. Davis
*Attorney, Agent, or Firm*—James R. Hoatson, Jr.; Richard D. Stone; William H. Page, II

[57] ABSTRACT

A process for the separation of butene-1 from other C4 mono-olefins. A feed stream containing butene-1 is contacted with a K-X zeolite which selectively adsorbs butene-1. The butene-1 is desorbed using a mixture of hexene-1 and cyclohexene or cyclohexane.

13 Claims, No Drawings

DESORBENT FOR SEPARATION OF BUTENE-1 FROM A C4 HYDROCARBON MIXTURE USING ZEOLITE X

BACKGROUND OF THE INVENTION

1. Field of the Invention

The invention relates to hydrocarbon separation, specifically the separation of butene-1 from a feed mixture containing other C4 mono-olefins using a potassium exchanged type X zeolite.

2. Description of the Prior Art

It is known from U.S. Pat. No. 3,723,561 (Class 260/677AD), the contents of which are incorporated by reference, to separate butene-1 from hydrocarbon mixtures using zeolites X and Y.

The present invention is an improvement on the process described in that patent. The improvement is the discovery of a better desorbent for the process.

The teachings of this patent as to the types of desorbents which can be used are very broad, and include many desorbents which although operable are not as good as the desorbent claimed herein.

The prior patent mentioned, as specific desorbent materials which could be used, higher molecular weight olefins such as octene-1 or lower molecular weight olefins. All of these were capable of separation from butene-1. The use of mixtures of normal olefins and iso-paraffins was also disclosed, with a mixture of 20 LV% octene-1 and 80 LV% iso-octane being disclosed at column 4, lines 50-53. This was the desorbent of choice for liquid phase operations.

Extensive studies of various adsorbents taught in that patent showed that a potassium exchanged X-zeolite gave excellent results. Further testing of different batches of experimental adsorbents was conducted to confirm that different manufacturing procedures could be used.

In the course of the testing of these adsorbents produced by conventional methods, there were some surprising discrepancies in results. Repeating the tests, we noted that not all the test conditions were the same, specifically that the feed composition varied somewhat test to test, and also that the desorbent composition varied as well.

Further testing showed that the desorbent composition had a significant effect on the process. It was discovered that use of a cyclo-paraffin or cyclo-olefin diluent with the preferred hexene-1 desorbent gave a desorbent with ideal properties for commercial use.

SUMMARY OF THE INVENTION

Accordingly, the present invention provides a process for separating butene-1 from a feed containing butene-1 and other C4 hydrocarbons, which process comprises the steps of: (a) contacting said feed with a type X zeolite containing potassium cations to effect selective adsorption of butene-1 by said adsorbent; (b) contacting said adsorbent containing adsorbed butene-1 with a desorbent consisting of 90 to 10 LV% of a mono-olefin having a molecular weight greater than said feed, and 10 to 90 LV% of a desorbent component selected from the group of cyclohexene and cyclohexane and mixtures thereof, thereby displacing said butene-1 from said adsorbent.

In another embodiment, the present invention provides a process for separating butene-1 from a feed containing butene-1 and other C4 hydrocarbons using an adsorbent comprising an X zeolite containing potassium cations, which process comprises the steps of: (a) maintaining net fluid flow through a column of said adsorbent in a single direction, which column contains at least three separate and serially interconnected zones; (b) maintaining an adsorption zone defined by the feed inlet and raffinate outlet as a downstream boundary; (c) maintaining a purification zone defined by an extract outlet and said feed inlet as a downstream boundary; (d) maintaining a desorption zone defined by a desorbent inlet and said extract outlet as a downstream boundary; (e) passing said feed into said adsorption zone at adsorption conditions and adsorbing said butene-1 and withdrawing a raffinate stream; (f) passing a desorbent comprising 10 to 90 LV% hexene-1 and 90 to 10 LV% cyclohexane or cyclohexene into said desorption zone at desorption conditions and displacing said butene-1 from said adsorbent; (g) withdrawing an extract stream comprising said butene-1 and desorbent from said desorption zone; and, (h) periodically advancing through said column of adsorbent in a downstream direction with respect to fluid flow said feed inlet, raffinate outlet, desorbent inlet, and extract outlet to shift zones through said adsorbent.

DETAILED DESCRIPTION OF THE INVENTION

The adsorbent which can be used in the process of this invention is a type X zeolite which has been ion exchanged to contain potassium. In the prior patent it was taught that either a type X or a type Y zeolite could be used. We believe that the desorbent we have discovered may be useful with other adsorbent systems, but it is extremely difficult to predict this. The effectiveness of the desorbent seems to be bound up with the properties of the adsorbent in some as yet not clearly understood fashion.

The desorbent must displace the adsorbed species from the molecular sieve. The desorbent must itself be fairly easily displaceable from the adsorbent, so that the molecular sieve can be reused in the process.

In a preferred embodiment, the butene-1 separation process occurs over a simulated moving bed of adsorbent. It is in this application where desorbent properties become extremely important, because a desorbent which will not readily displace the adsorbate butene-1 from the adsorbent will require use of great amounts of desorbent. This is undesirable because quite a lot of energy is used to separate butene-1 from the desorbent, which permits reuse of the desorbent in the process. It is also undesirable if the desorbent is held too tenaciously by the adsorbent, because then it is difficult to load up the adsorbent with butene-1. This can be compensated by providing more zones in a simulated moving bed or an extra amount of contact time between feed and adsorbent, which is soaked in desorbent, to permit the adsorbent to adsorb the desired butene-1 species.

Feed streams which can be used in this invention can include any of those mentioned in the prior patent. In testing of this process experimentally four different feeds were used, which primarily reflected the availability of different feeds at different test facilities.

Feed A consists of the feed material described in U.S. Pat. No. 3,723,561, Example I. These feed mixtures were not available for the present tests.

Feed B consists of:
2.3 LV% iC4
5.9 LV% nC4

35.1 LV% butene-1
46.4 LV% isobutylene
10.3 LV% t-butene-2

Feed is displaced from a 3 cc sample loop, using desorbent, and injected into an adsorbent bed consisting of 70 cc adsorbent in a 5 foot × ⅜ inch stainless steel tube.

Feed C consists of:
33 LV% nC4
26 LV% butene-1
19 LV% isobutylene
22 LV% cis and trans butene-2

Feed is diluted with 75 cc of desorbent per 25 cc of feed, and 10 cc of this mixture fed into an adsorbent bed consisting of 70 cc adsorbent in a 5 foot × ⅜ inch stainless steel tube.

Feed D consists of:
44 LV% nC4
42 LV% butene-1
14 LV% isobutylene

Feed is displaced from a 3 cc sample loop, using desorbent, and injected into an adsorbent bed consisting of 70 cc of adsorbent in a 5 foot × ⅜ inch stainless steel tube.

Several adsorbents were used. All were K exchanged type X zeolites. The zeolites were originally Na-X, and then ion-exchanged with K using conventional techniques, such as disclosed in U.S. Pat. No. 3,723,561. It is believed that almost complete ion-exchange, more than 95%, of K for Na occurred. As a check, one adsorbent was given a double ion exchange treatment, but no significant difference in characteristics was observed.

In testing different feeds, some differences in performance were noted. Attempts were made to duplicate earlier results and it was learned that the desorbent composition had a profound effect on operation of the process. The active desorbent ingredient was thought to be an olefin of different boiling point, with hexene-1 being the preferred desorbent. This material was diluted in a normal paraffin which was considered inert. Testing of two different adsorbents showed some surprising results one worked well and the other did not, but both were K-X adsorbents.

The tests were originally conducted to see if two different K-X adsorbents were equivalent. Retesting confirmed that the adsorbents were, but the desorbents were not. The test results are reported in the following tables.

The tests were all conducted at 50° C. The adsorbents used were all K-X, as previously discussed though obtained from different sources. It is believed that all K-X adsorbents tested were roughly equivalent, but nonetheless the experimental adsorbent number is included to indicate when the same adsorbent was used in several tests.

EXAMPLE I

A test was conducted using Feed B.
The desorbent was 25 LV% hexene-1 in n-C6.

TABLE I

| Adsorbent | SIV-1-96 | SIV-1-97 |
|---|---|---|
| Peak Widths, cc, for: | | |
| n-Butane | 9.70 | 6.88 |
| Butene-1 | 20.1 | 17.2 |
| Isobutylene | 19.5 | 16.5 |
| t-Butene-2 | 17.5 | 16.0 |
| c-Butene-2 | — | — |
| Selectivities: | | |
| Butene-1/isobutylene | 2.06 | 2.07 |
| Butene-1/t-Butene-2 | 3.24 | 3.10 |
| Butene-1/c-Butene-2 | — | — |
| Butene-1 Retention Vol. cc | 35.6 | 34.7 |

The peak widths are an indication of mass transfer rates or the rate of counter diffusion between the adsorbed molecule and the desorbent. In general wide peak widths are indicative of slow counter diffusion rates and conversely narrow peaks indicate fast rates. The limiting peak width with respect to narrowness is that of the n-butane which is essentially unadsorbed. Thus, the closer the peak widths of the adsorbed olefin molecules are to the unadsorbed tracer the better the adsorbent-desorbent system.

Selectivity is roughly equivalent to the term relative volatility in distillation, and is an indication of how efficient an adsorbent is at separating different species. For a successful commercial separation, a selectivity of at least about 2.0 is usually required. A lower selectivity requires a large inventory of adsorbent, to make the separation. High selectivities reduce the adsorbent inventory required.

The retention volume of butene-1 is a qualitative indication of the selectivity between the butene-1 and desorbent. A large retention volume indicates that the selectivity of butene-1 with respect to the desorbent is high and conversely, a short retention volume indicates it is low. In general, for the test conditions described here, the butene-1 retention volume should have a value that lies between 20 and 13 cc. A value less than about 13 cc means that the selectivity for butene-1 with respect to the desorbent is less than unity which is undesirable, supra vide. A value greater than about 20 cc indicates that too much desorbent is required to desorb the butene-1.

EXAMPLE II

These tests were repeated on a different adsorbent, i.e., a fresh batch of K-X adsorbent, SIV-1-154. A sample of the SIV-1-154 adsorbent was given a second ion exchange treatment with K, and designated as SIV-1-164C. Note that for all of these tests the desorbent was hexene-1 in n-C7. In contrast, desorbent in Example I was hexene-1 in n-C6.

TABLE II

| Adsorbent | SIV-1-154 | SIV-1-164C | | |
|---|---|---|---|---|
| Desorbent | 20% Hexene-1 in n-C7 | 20% Hexene-1 in n-Heptane | 25% Hexene-1 in n-Heptane | 25% Hexene-1 in n-Heptane |
| Feed | Feed C | Feed C | Feed C | Feed D |
| Pk Envelope Widths cc for: | | | | |
| n-Butane | 10.6 | 10.3 | 11.5 | 11.3 |
| Butene-1 | 16.7 | 16.6 | 15.3 | 15.9 |
| Isobutylene | 14.1 | 12.5 | 11.8 | 11.3 |
| t-Butene-2 | 14.3 | 15.4 | 13.3 | — |
| c-Butene-2 | 15.3 | 14.0 | 11.4 | — |
| Selectivities for: | | | | |
| Butene-1/isobutane | 1.64 | 1.65 | 1.65 | 1.64 |
| Butene-1/t-Butene-2 | 2.50 | 2.62 | 2.42 | — |

TABLE II-continued

| Adsorbent | SIV-1-154 | SIV-1-164C | | |
|---|---|---|---|---|
| Desorbent | 20% Hexene-1 in n-C$_7$ | 20% Hexene-1 in n-Heptane | 25% Hexene-1 in n-Heptane | 25% Hexene-1 in n-Heptane |
| Feed | Feed C | Feed C | Feed C | Feed D |
| Butene-1/c-Butene-2 | 1.93 | 1.98 | 1.96 | — |
| Butene-1 Retention Vol cc | 43.21 | 41.56 | 36.78 | 33.52 |

Example I shows that a desorbent of 25 LV% hexene-1 in n-C$_6$ is satisfactory as far as selectivity goes, but the butene-1 retention volume is unacceptably high (35.6 and 34.7 cc), also, the counter diffusion rates are poor as manifested by the wide peak widths.

Example II indicates that substituting n-C$_7$ for n-C$_6$ results in a process which is unacceptable, from a selectivity viewpoint, and because of an undesirably large butene-1 retention volume. These experiments suggested that there was quite an effect due to the use of different diluents in the desorbent, and suggested that the use of normal paraffin diluents, and certainly n-C$_7$, as a diluent in this system was undesirable.

EXAMPLE III

Tests were then made to see if the method of adding the feed sample was having a significant effect. In one instance the feed is diluted to 25 LV% concentration in desorbent and introduced as a 10 cc pulse into the adsorption column. In the other type of sample injection procedure, the feed is introduced in undiluted form from a 3 cc sample loop into the adsorbent column, using desorbent to displace the feed into the column. Test results are reported on the following tables:

TABLE III

| Adsorbent | SIV-1-164C | | 3043-22 | |
|---|---|---|---|---|
| Desorbent | 25% Hexene-1 in n-Heptane | | | |
| Feed | Feed C (Diluted) | Feed D (Undiluted) | Feed C (Diluted) | Feed D (Undiluted) |
| Peak Envelope Widths cc | | | | |
| n-Butane | 11.3 | 8.9 | 11.1 | 9.8 |
| Butane-1 | 16.2 | 18.0 | 17.2 | 17.1 |
| Isobutylene | 13.1 | 15.0 | 11.4 | 12.3 |
| t-Butene-2 | 15.8 | — | 12.1 | — |
| c-Butene-2 | 13.7 | — | 10.3 | — |
| Selectivity for: | | | | |
| Butene-1/Isobutylene | 1.65 | 1.83 | 1.72 | 1.79 |
| Butene-1/t-Butene-2 | 2.46 | — | 3.02 | — |
| Butene-1/c-Butene-2 | 2.04 | — | 2.05 | — |
| Butene-1 Retention Vol. cc | 36.68 | 32.97 | 36.93 | 31.24 |

EXAMPLE IV

Tests were run to see the effect of non-normal compounds as desorbents. Pure iso-octane and pure cyclohexane were each tested. The experimental results are reported on the following Table IV.

TABLE IV

| Adsorbent | SIV-1-97 | | |
|---|---|---|---|
| Feed | Feed B 25% Hexene-1 in n-C$_6$ | Feed B 100% Iso-octane | Feed B 100% Cyclohexane |
| Desorbent | | | |
| Pk Envelope Widths cc: | | | |
| n-Butane | 9.70 | 18.3 | 20.1 |
| Butene-1 | 20.1 | 70.8 | 53.6 |
| Isobutylene | 19.5 | 31.0 | 26.1 |
| t-Butene-2 | 17.5 | 28.8 | 35.8 |
| Selectivities for: | | | |
| Butene-1/Isobutylene | 2.06 | 3.12 | 3.48 |
| Butene-1/t-butene-2 | 3.24 | 3.06 | 1.78 |
| Butene-1 Retention Vol cc | 35.6 | 72.1 | 34.5 |

It can be seen from the data in this Table that iso-octane is a superior desorbent as far as selectivities go, but is poor in terms of the butene-1 retention volume. The iso-octane does not displace butene-1 from the adsorbent quickly enough to permit its use in a commercial process.

Pure cyclohexane presents a quite different selectivity pattern, but again does not desorb butene-1 quickly enough, as evidenced by the butene-1 retention volume, to permit its use commercially. Pure cyclohexane also suffers in that the selectivity for butene-1 relative to t-butene-2 is unacceptably low.

EXAMPLE V

To determine if a commercially viable desorbent could be obtained, another series of tests was run on a K-X zeolite using mixtures of hexene-1 in various diluents, mainly cyclohexene and cyclohexane. For comparison purposes, tests using pure hexene-1 and pure cyclohexene were also used. These are reported in Table V.

TABLE V

| Adsorbent | ← | ← | ← | 3043-22 → | → | → |
|---|---|---|---|---|---|---|
| Feed | ← | ← | ← | Feed C → | → | → |
| Desorbent | 25% Hexene-1 in Cyclohexane | 100% Hexene-1 | 100% Cyclohexene | 50% Hexene-1 50% Cyclohexene | 50% Hexene-1 50% Cyclohexane | 75% Hexene-1 25% Cyclohexane |
| Pk. Env. Widths cc: | | | | | | |
| n-Butane | 10.6 | 10.2 | 9.5 | 11.2 | 10.3 | 10.0 |
| Butene-1 | 16.2 | 11.5 | 16.1 | 13.3 | 12.8 | 11.7 |
| Isobutylene | 12.9 | 10.6 | 11.1 | 11.7 | 11.7 | 10.8 |
| t-Butene-2 | 10.0 | 10.7 | 12.0 | 11.6 | 12.2 | 10.4 |
| c-Butene-2 | 12.2 | 10.3 | 11.7 | 11.2 | 11.5 | 10.8 |
| Selectivities for: | | | | | | |
| Butene-1/Isobutylene | 2.36 | 1.81 | 3.23 | 2.68 | 2.25 | 2.06 |
| Butene-1/t-butene-2 | 1.95 | 3.93 | 1.41 | 2.43 | 3.10 | 3.31 |
| Butene-1/c-butene-2 | 2.86 | 2.45 | 2.98 | 3.18 | 2.90 | 2.70 |
| Butene-1 Retention Vol cc | 32.72 | 14.99 | 22.80 | 17.73 | 20.19 | 16.39 |

From these test results, we determined that two different desorbent compositions were optimum. When an olefinic cyclic diluent was used, the optimum concentration of each component, hexene-1 and cyclohexene, was about 50 LV%. This mixture gave a desorbent which produced very high selectivities of butene-1 for isobutylene and cis and trans butene-2. The butene-1 retention volume was a very satisfactory 17.73 cc.

Surprisingly when cyclohexane was used as a diluent in the desorbent, instead of cyclohexene, a different composition appears optimum. Thus the 50/50 mixture of hexene-1 cyclohexane produced a desorbent which gave good selectivities, but the butene-1 retention volume was somewhat higher than preferred. Use of a mixture of 75% hexene-1 and 25% cyclohexane produced a desorbent with very desirable properties regards butene-1 retention volume, with a figure of 16.39 cc which is significantly lower than the butene-1 retention volume of the 50/50 mixture of hexene-1 in cyclohexane. The selectivities obtained with a desorbent of 75% hexene-1 and 25% cyclohexane are all satisfactory.

Commercially use of cyclohexane as a diluent is preferred, but this is due more to its ready availability and low cost than to any great advantage over the use of cyclohexene diluent.

Although not preferred, it is possible to have a workable process when using as little as 10 LV% or as much as 90 LV% of the cyclic desorbent component, i.e. cyclohexane or cyclohexene.

We claim as our invention:

1. A process for separating butene-1 from a feed containing butene-1 and other $C_4$ hydrocarbons, which process comprises the steps of:
    (a) contacting said feed with a type X zeolite containing potassium cations to effect selective adsorption of butene-1 by said adsorbent;
    (b) contacting said adsorbent containing adsorbed butene-1 with a desorbent comprising 90 to 10 LV% of hexene-1 and 10 to 90 LV% of a desorbent component selected from the group of cyclohexene and cyclohexane and mixtures thereof, thereby displacing said butene-1 from said adsorbent.

2. Process of claim 1 wherein said desorbent component is cyclohexene.

3. Process of claim 2 wherein the desorbent is 50 LV% hexene-1 and 50 LV% cyclohexene.

4. Process of claim 1 wherein said desorbent component is cyclohexane.

5. Process of claim 4 wherein the desorbent is 75% hexene-1 and 25 LV% cyclohexane.

6. A process for separating butene-1 from a feed containing butene-1 and other $C_4$ hydrocarbons using an adsorbent comprising an X zeolite containing potassium cations, which process comprises the steps of:
    (a) maintaining net fluid flow through a column of said adsorbent in a single direction, which column contains at least three separate and serially interconnected zones;
    (b) maintaining an adsorption zone defined by the feed inlet and raffinate outlet as a downstream boundary;
    (c) maintaining a purification zone defined by an extract outlet and said feed inlet as a downstream boundry;
    (d) maintaining a desorption zone defined by a desorbent inlet and said extract outlet as a downstream boundary;
    (e) passing said feed into said adsorption zone at adsorption conditions and adsorbing said butene-1 and withdrawing a raffinate stream;
    (f) passing a desorbent comprising 10 to 90 LV% hexene-1 and 90 to 10 LV% cyclohexane of cyclohexene into said desorption zone at desorption conditions and displacing said butene-1 from said adsorbent;
    (g) withdrawing an extract stream comprising said butene-1 and desorbent from said desorption zone; and,
    (h) periodically advancing through said column of adsorbent in a downstream direction with respect to fluid flow said feed inlet, raffinate outlet, desorbent inlet, and extract outlet to shift zones through said adsorbent.

7. Process of claim 6 wherein at least a portion of the raffinate stream is passed to a separation means wherein at least a portion of said desorbent is removed from said stream to produce raffinate product having a reduced desorbent content.

8. Process of claim 6 wherein at least a portion of said extract stream is passed to a separation means wherein at least a portion of said desorbent is removed from said stream to produce extract product having reduced desorbent content.

9. Process of claim 6 wherein a buffer zone is maintained immediately upstream from said desorption zone, said buffer zone defined as the adsorbent located between the desorbent inlet in a downstream boundary of said buffer zone and a raffinate outlet at an upstream boundary of said buffer zone.

10. Process of claim 6 wherein the desorbent is a mixture of hexene-1 and cyclohexene.

11. Process of claim 10 wherein the desorbent is 50 LV% hexene-1 and 50 LV% cyclohexene.

12. Process of claim 6 wherein the desorbent is a mixture of hexene-1 and cyclohexane.

13. Process of claim 12 wherein the desorbent is 75% hexene-1 and 25 LV% cyclohexane.

* * * * *